(12) United States Patent
Mizota et al.

(10) Patent No.: US 9,423,380 B2
(45) Date of Patent: Aug. 23, 2016

(54) ULTRASONIC INSPECTION METHOD, ULTRASONIC TEST METHOD AND ULTRASONIC INSPECTION APPARATUS

(71) Applicant: Hitachi, Ltd., Chiyoda-ku, Tokyo (JP)

(72) Inventors: Hirohisa Mizota, Hitachi (JP); Naoyuki Kono, Mito (JP)

(73) Assignee: Hitachi, Ltd., Tokyo (JP)

( * ) Notice: Subject to any disclaimer, the term of this patent is extended or adjusted under 35 U.S.C. 154(b) by 851 days.

(21) Appl. No.: 13/652,941

(22) Filed: Oct. 16, 2012

(65) Prior Publication Data

US 2013/0151171 A1    Jun. 13, 2013

(30) Foreign Application Priority Data

Oct. 17, 2011  (JP) .................................. 2011-227903

(51) Int. Cl.
```
G01N 29/24      (2006.01)
G06F 17/00      (2006.01)
G01N 29/06      (2006.01)
G01N 29/265     (2006.01)
```

(52) U.S. Cl.
CPC .............. *G01N 29/24* (2013.01); *G01N 29/069* (2013.01); *G01N 29/265* (2013.01); *G06F 17/00* (2013.01)

(58) Field of Classification Search
CPC ........................... G01N 29/262; G10K 11/345
USPC .............. 702/36; 73/598, 600, 602, 622, 627, 73/628
See application file for complete search history.

(56) References Cited

U.S. PATENT DOCUMENTS

| 2003/0079545 A1 | 5/2003 | Matney et al. |
| 2006/0230831 A1 | 10/2006 | Berke |
| 2007/0000328 A1 | 1/2007 | Buttram |
| 2009/0007678 A1* | 1/2009 | Fukutomi et al. ............... 73/598 |

(Continued)

FOREIGN PATENT DOCUMENTS

| JP | 1-145565 A | 6/1989 |
| JP | 11-326297 A | 11/1999 |

(Continued)

OTHER PUBLICATIONS

"Measurement of Flaw Height Using Tip Echo Technique", Standard of the Japanese Society for Non-Destructive Inspection (NDIS), NDIS 2418, Sep. 26, 2005 (twenty-four (24) sheets).

(Continued)

*Primary Examiner* — Michael Nghiem
*Assistant Examiner* — Peter Ngo
(74) *Attorney, Agent, or Firm* — Crowell & Moring LLP

(57) ABSTRACT

The invention is directed to an ultrasonic inspection method, an ultrasonic test method, and an ultrasonic inspection apparatus that enable sizing to be executed even for a minute defect using an ultrasonic wave. A holder holds a transmitting probe for executing an angle beam method and a receiving probe for executing a vertical beam method. A motor and a guide rail form a movement mechanism for the transmitting probe and the receiving probe. In an ultrasonic test mode, the transmitting probe executes the angle beam method and transmits and receives an ultrasonic wave. In a sizing mode, the transmitting probe transmits an ultrasonic wave and the receiving probe receives this wave. A tip echo of a wave diffracted from a tip of a defect on a sample and a corner echo reflected from a corner of the defect are measured from a waveform received by the receiving probe.

3 Claims, 13 Drawing Sheets

(56) References Cited

U.S. PATENT DOCUMENTS

| | | |
|---|---|---|
| 2009/0095085 A1 | 4/2009 | Koinuma |
| 2009/0199642 A1 | 8/2009 | Fukutomi et al. |
| 2009/0308163 A1 | 12/2009 | Fukutomi et al. |
| 2010/0251821 A1* | 10/2010 | Mizota et al. .................. 73/602 |

FOREIGN PATENT DOCUMENTS

| | | |
|---|---|---|
| JP | 2001-27630 A | 1/2001 |
| JP | 2006-113044 A | 4/2006 |
| JP | 2007-315820 A | 12/2007 |
| JP | 2009-97889 A | 5/2009 |
| JP | 2009-156834 A | 7/2009 |
| JP | 2010-276465 A | 12/2010 |

OTHER PUBLICATIONS

"Method of Measuring Defect Height by Using TOFD Technique", Standard of the Japanese Society for Non-Destructive Inspection (NDIS), NDIS 2423, Jul. 18, 2001 (fourteen (14) sheets).

"Ultrasonic Test Method", pp. 248-255 (four (4) sheets).

"Introduction to Phased Array Ultrasonic Technology Applications", Main Formulas and Ultrasonic Reference Data, chapter 2, pp. 80-87 (four (4) sheets).

Japanese Office Action dated May 19, 2015 (Three (3) pages).

\* cited by examiner

FIG. 11

| FOCAL POINT F(i) | ELEMENT NUMBER | GAIN | 1 | | ... | | M | | M+1 | | ... | | M+N | | |
|---|---|---|---|---|---|---|---|---|---|---|---|---|---|---|---|
| | | | P | R | | | P | R | P | R | | | P | R | |
| i = 1 | | G1 | T1,1 | R1,1 | ... | ... | T1,M | R1,M | -1 | -1 | ... | ... | -1 | -1 | ⎫ NORMAL ANGLE BEAM METHOD |
| ... | | | ... | ... | ... | ... | ... | ... | ... | ... | ... | ... | ... | ... | |
| i = k | | | Tk,1 | Rk,1 | ... | ... | Tk,M | Rk,M | -1 | -1 | ... | ... | -1 | -1 | ⎭ |
| i = k+1 | | G2 | Tk+1,1 | -1 | ... | ... | Tk+1,M | -1 | -1 | R k+1, M+1 | ... | ... | -1 | R k+1, M+N | ⎫ ULTRASONIC TEST METHOD FOR SIZING |
| ... | | | ... | ... | ... | ... | ... | ... | ... | ... | ... | ... | ... | ... | |
| i = k+1 | | | Tk+1,1 | -1 | ... | ... | Tk+1,M | -1 | -1 | R k+1, M+1 | ... | ... | -1 | R k+1, M+N | ⎭ |

P : PULSAR
R : RECEIVER

1–M : ELEMENTS OF TRANSMITTING PROBE
M+1–M+N : ELEMENTS OF RECEIVING PROBE

ULTRASONIC INSPECTION METHOD, ULTRASONIC TEST METHOD AND ULTRASONIC INSPECTION APPARATUS

BACKGROUND OF THE INVENTION

1. Field of the Invention

The present invention relates to an ultrasonic inspection method, an ultrasonic test method and an ultrasonic inspection apparatus. The invention more particularly relates to an ultrasonic inspection method, an ultrasonic test method and an ultrasonic inspection apparatus which are suitable to evaluate the height of a minute defect.

2. Description of the Related Art

Many metal devices and structures exist in electric power plants and chemical plants. Cracks (defects) such as fatigue cracks and stress corrosion cracking may occur on the surfaces of metal devices and structure and develop inside the plants. In order to ensure the soundness of the metal devices and structures, it is necessary to execute a non-destructive inspection; a visual inspection, an inspection with radiation transmission, an ultrasonic inspection and the like are executed for that purpose. In addition, there is an increasing demand to not only determine the presence or absence of a defect but also accurately evaluate the height of a defect developing in the metal devices and structures.

For a main pipe and the like of the power generating plant, for example, part at which a crack is likely to occur and direction in which the crack will develop can be estimated to some extent by stress analysis or the like though they vary depending on a substance, an environment, stress and the like. In contrast, when the ultrasonic inspection is used, it is difficult to visualize the details of the defect. If a wave reflected from an edge (aperture of a defect) at which the defect has occurred is detected by the ultrasonic inspection, however, then the degree of development of the defect in a sample can be evaluated by carefully detecting a wave diffracted from the distal end of the defect. Thus, emphasis is placed on an ultrasonic inspection whose inspection system is relatively simple is used and that enables information on the inside of the structure almost to be acquired.

Conventional ultrasonic inspection methods for sizing include a single probe method (conventional method) and a double-probe method. The single probe method is an inspection method for transmitting and receiving an ultrasonic wave by the same probe using a probe (hereinafter referred to as single probe) provided with a single element or a probe (hereinafter referred to as array probe) provided with multiple elements. The double-probe method is an inspection method for transmitting and receiving an ultrasonic wave by combined two probes, which are a probe for transmitting an ultrasonic wave and a probe for receiving an ultrasonic wave (refer to, for example, Non-Patent Document 1, "Method for measuring the height of a defect using tip echo method" issued by The Japanese Society for Non-Destructive Inspection, on Jun. 1, 1997). Two units of a single probe or two units of an array probe may be combined as the probes to be used for the double-probe method. A single probe and an array probe may be combined. The conventional single probe method to be used for sizing is an angle beam method. The angle beam method is to cause an ultrasonic wave transmitted by a single angle probe or an array probe to be incident on a surface (to be inspected) in an oblique direction, cause the same probe to receive a wave (corner echo) reflected from an aperture of the defect and a wave (tip echo) diffracted from the tip of the defect, locate the position of the probe receiving the waves with the maximum intensities, and evaluate the height of the defect from the path lengths of the diffracted wave and the reflected wave.

Proposed conventional double-probe methods include a TOFD method, an SPOD method, a delta method, and a CAFS method.

Sizing based on the TOFD method is as follows. A transmitting probe and a receiving probe are arranged so that the defect lies between the transmitting probe and the receiving probe, an ultrasonic wave is transmitted and received therebetween, and a diffracted wave is received, thereby evaluating the height of a defect (refer to, for example, Non-Patent Document 2, "Method for measuring the height of a defect using TOFD method" issued by the Japanese Society for Non-Destructive Inspection, on Dec. 1, 2001).

Sizing based on the SPOD method is as follows. An angle probe is used as a transmitting probe so as to transmit an ultrasonic wave at an oblique angle while a vertical probe is used as a receiving probe so as to receive the ultrasonic wave in a vertical direction. The ultrasonic wave transmitted from the angle probe is incident on a defect in an oblique direction so as to cause a wave to be diffracted from the tip of the defect. The vertical probe located above the defect receives a diffracted wave directly propagating above the defect and a diffracted wave reflected (skipped) on a back surface once and propagating above the defect after the reflection, and thus the height of the defect from the back surface of the tip of the defect is evaluated based time periods for the propagations of the diffracted waves (refer to, for example, JP-2007-315820-A).

Sizing based on the delta method is one of mode conversion methods and is as follows. An angle probe is used as a transmitting probe so as to transmit an ultrasonic wave at an oblique angle while a vertical probe is used as a receiving probe so as to receive the ultrasonic wave in a vertical direction in the same manner as the SPOD method. The angle probe transmits a 60-degree transverse wave. The vertical probe receives a 0-degree longitudinal diffracted wave subjected to mode conversion at the tip of the defect after being skipped at a back surface, and thus the height of the defect is evaluated (refer to, for example, Non-Patent Document 3, "Ultrasonic test method, P. 249, (issued on Jul. 30, 1974 by The Nikkan Kogyo)" and Non-Patent Document 4, "Introduction to phased array ultrasonic technology applications, P. 84 (issued in August, 2004 by R/D Tech Inc.)".

SUMMARY OF THE INVENTION

In general, the intensity of a tip echo that is a wave diffracted from a tip of a defect is significantly lower than the intensity of a corner echo that is a wave reflected from an aperture of the defect. Thus, if the defect is minute, paths in which the echoes appear are close, and the echoes cannot be separated from each other in some cases. In a welded part, the intensity of a signal of a tip echo may be reduced due to scattering of crystal grains. In addition, noise with an intensity that is equal to or nearly equal to the intensity of the tip echo may occur at a welding boundary. Thus, a signal-to-noise ratio may be reduced, and the tip echo may not be detected.

When the angle beam method using a single probe is used, the ratio of the intensity of a corner echo to the intensity of a tip echo is large and the tip echo is hidden by the corner echo. Thus the height of a minute defect cannot be evaluated.

According to the TOFD method described in Non-Patent Document 2, the transmitting and receiving probes are arranged so as to sandwich a defect. Thus, a propagation path for a diffracted wave is long. It is difficult to capture a low-intensity diffracted wave when a welded part or a thick material is inspected.

When the SPOD method described in JP-A-2007-315820 is employed, a propagation path for a diffracted wave that propagates after being reflected on a back surface once is long although the problem with the propagation path in the TOFD method can be remedied. In addition, the intensity of a wave reflected in a desired direction is not sufficient depending on the shape of a sample. As a result, the intensity of a signal is likely to be low.

The delta method described in Non-Patent Documents 3 and 4 uses not a simple reflected wave but a mode-converted ultrasonic wave, although the problem with the propagation path in the TOFD method can be remedied. Thus, the wave is affected by the shape of a sample, like the SPOD method. If the sound speed of the wave is constant, a path cannot be properly displayed in waveform data that is displayed as an inspection result. Thus, waveform evaluation is difficult and a formula for evaluating the height of a defect is complex.

When the height of a minute defect is evaluated using a conventional method by an inspector, the evaluation largely depends on skills of the inspector. It has been necessary to improve an ultrasonic test method, a method for evaluating a waveform and a method for displaying a signal.

An object of the present invention is to provide an ultrasonic inspection method, an ultrasonic test method and an ultrasonic inspection apparatus, which use an ultrasonic wave to accurately and simply execute sizing even for a minute defect.

(1) In order to accomplish the aforementioned object, according to the invention, an ultrasonic test method includes the steps of: arranging a probe capable of executing an angle test method as a transmitting probe at a position at which the transmitting probe can transmit an ultrasonic wave to a defect at an oblique angle; arranging a probe capable of executing a vertical beam method as a receiving probe at a position at which the receiving probe can receive the ultrasonic wave from the defect in a vertical direction; causing the ultrasonic wave transmitted by the transmitting probe to be incident on the defect; measuring a tip echo of a wave diffracted from a tip of the defect and a corner echo reflected from a corner of the defect; and calculating the difference between path lengths of the echoes.

The ultrasonic test method enables sizing to be accurately and simply executed on a minute defect using an ultrasonic wave.

(2) In Item (1), it is preferable that the height of the defect be calculated using a value of $(h/(1+\cos \alpha))$, where h is the difference between the path lengths and $\alpha$ is an angle between a direction in which the defect develops and a direction in which the ultrasonic wave is transmitted.

(3) In Item (1), it is preferable that the probes be array probes, and the height of the defect be calculated using a value of $(h/1+(\cos((\theta 1+\theta 2)/2)/\cos((\theta 2-\theta 1)/2)))$ $(h/(1+\cos \alpha))$, where h is the difference between the path lengths, $\theta 1$ is a refraction angle causing the intensity of the corner echo to be maximal, and $\theta 2$ is a refraction angle causing the intensity of the tip echo to be maximal.

(4) In order to accomplish the aforementioned object, according to the invention, an ultrasonic inspection method includes: a first step of arranging a probe on a sample, starting an inspection and moving the probe; a second step of using only a transmitting probe to execute an angle beam method and detect a corner echo and thereby determining whether or not a defect exists; a third step of evaluating the position of the defect on the basis of path lengths displayed with a received waveform and a refraction angle if the corner echo has been detected; a fourth step of searching a tip echo using the angle beam method if the corner echo has been detected; a fifth step of arranging a receiving probe immediately above the basis of the position, obtained from the waveform, of the defect if the tip echo is not detected and detecting the corner echo and the tip echo; and a sixth step of executing sizing on the defect on the basis of the difference between the path length of the corner echo and the path length of the tip echo if the corner echo and the tip echo are detected.

The ultrasonic inspection method enables the sizing to be accurately and simply executed on a minute defect using an ultrasonic wave.

(5) In Item (4), it is preferable that in fourth step of searching the tip echo using the angle beam method, a threshold for an SN ratio of the detected tip echo be provided, and it be determined whether or not the detected tip echo has a sufficient intensity.

(6) In Item (4), it is preferable that the height of the defect be calculated using a value of (h−(Wia−Wit)), where h is the difference between the path lengths, Wia is a distance between a point at which an ultrasonic wave is incident on the sample and an aperture of the defect, and Wit is a distance between the point at which the ultrasonic wave is incident on the sample and a tip of the defect.

(7) In Item (4), it is preferable that the transmitting probe be an array probe, an angle at which an ultrasonic wave is transmitted be treated as a polar coordinate, the ultrasonic wave transmitted by the transmitting probe be incident on the sample, the path length of the tip echo of a wave diffracted from a tip of the defect and the path length of the corner echo reflected from a corner of the defect be treated as polar coordinates on the basis of the waveform received by the receiving probe, and intensities of the received waveform be mapped at corresponding positions and displayed in a sector form.

(8) In Item (4), it is preferable that the transmitting probe be an array probe, an ordinate indicate an angle at which an ultrasonic wave is transmitted by the array probe, an abscissa indicate the path length of the tip echo of a wave diffracted from a tip of the defect and the path length of the corner echo reflected from a corner of the defect, and intensities of the received waveform be mapped at corresponding positions and displayed as a two-dimensional image, while the path lengths are obtained by causing the ultrasonic wave transmitted by the transmitting probe to be incident on the sample and causing the receiving probe to receive the waveform.

(9) In order to accomplish the aforementioned object, according to the invention, an ultrasonic test apparatus includes: a holder that holds a transmitting probe capable of executing an angle beam method and a receiving probe capable of executing a vertical beam method; a movement mechanism that is capable of moving the transmitting probe and the receiving probe; a transceiver that executes an ultrasonic test mode in which the transmitting probe executes the angle beam method and thereby transmits and receives an ultrasonic wave and a sizing mode in which the transmitting probe transmits an ultrasonic wave and the receiving probe receives the ultrasonic wave; a controller that controls the transceiver and the movement mechanism; and a display unit that displays, stores and evaluates data obtained by the methods.

The ultrasonic test apparatus with the aforementioned configuration can accurately and simply execute the sizing on a minute defect using an ultrasonic wave.

(10) In Item (9), it is preferable that the transceiver include a pulsar that includes a transmission delay unit for delaying a transmission signal corresponding to one or more elements included in the probe by a delay time and a transmitter for transmitting an ultrasonic wave, and a receiver that includes an analog-to-digital converter for converting the received ultrasonic wave to a digital signal and a memory unit for delaying the received signal by a delay time, and the controller include a delay controller that controls the delay times, a summing unit that sums received signals, a multiplier that multiplies a signal obtained by summing the received signals by the summing unit by a value set on the basis of the ultrasonic test mode, and a computer for control and processing that stores the received signals and has a processor for processing data.

(11) In Item (9), it is preferable that an image obtained in the ultrasonic test mode and an image obtained in the sizing mode be separately adjusted using gains, and the gains be displayed on a screen.

(12) It is preferable that the ultrasonic inspection apparatus described in Item (9) further include a sound-absorbent material that fixes the position of the transmitting probe and the position of the receiving probe and is arranged between the transmitting probe and the receiving probe so that the ultrasonic wave transmitted by the transmitting probe propagates in a part other than the sample but is not received by the receiving probe when the sample is a pipe, a plate or the like and has a constant thickness.

According to invention, it is possible to accurately and simply execute the sizing on a minute defect using an ultrasonic wave.

BRIEF DESCRIPTION OF THE DRAWINGS

FIG. 11 is a diagram illustrating setting of an array probe included in the ultrasonic inspection apparatus according to the embodiment of the invention.

DESCRIPTION OF THE PREFERRED EMBODIMENTS

The configuration and operations of an ultrasonic inspection apparatus according to an embodiment of the invention will be described below with reference to FIGS. 1 to 15B.

First, divergence of an ultrasonic wave is described.

Figure 1:
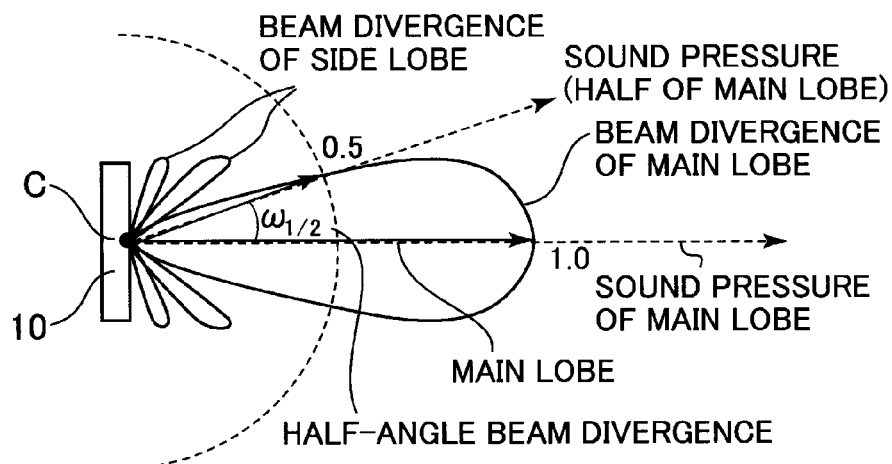
FIG. 1 is a diagram illustrating divergence of an ultrasonic wave.

FIG. 1 is a diagram illustrating the divergence of the ultrasonic wave.

The divergence of the ultrasonic wave from the center C of an ultrasonic oscillation element 10 can be represented by the following Formula (1) using an effective probe diameter Aeff and a wavelength λ of the wave within a sample.

$$\overline{\omega}_{1/2} \approx \arcsin(0.6\lambda/A_{eff}) \qquad (1)$$

In Formula (1), $\overline{\omega}_{1/2}$ is called a half-angle beam divergence and indicates an angle of a wave with sound pressure that is a half of the highest sound pressure (main lobe) among a main spatial angular distribution (main lobe) of an ultrasonic wave transmitted from the single element. As the value $\overline{\omega}_{1/2}$ is reduced, a beam distribution becomes sharper (or the wave has high directivity).

Next, a wave reflected on a defect by incidence of an ultrasonic wave on a sample is described with reference to FIG. 2.

Figure 2:
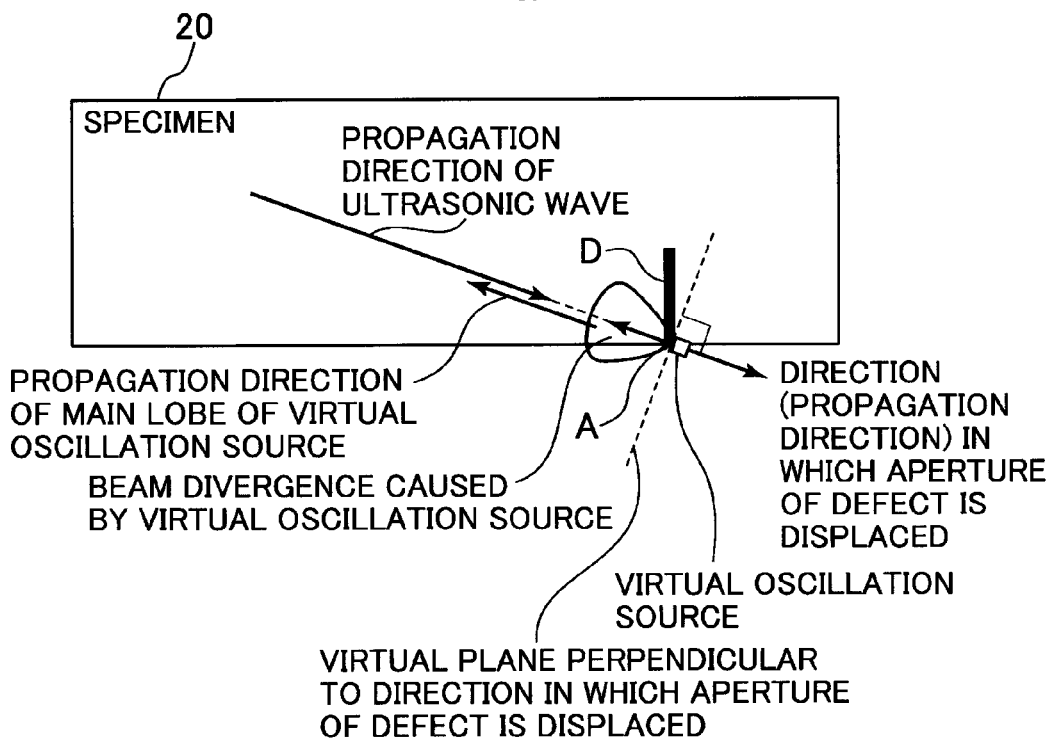
FIG. 2 is a diagram illustrating a wave reflected on a defect by incidence of an ultrasonic wave.

FIG. 2 is a diagram illustrating the wave reflected on the defect by the incidence of the ultrasonic wave.

A sample 20 is a flat plate and has a defect D therein. The defect D has an aperture A on the side of the bottom surface of the sample 20. The defect D develops internally of the sample 20 (in a direction from the bottom surface illustrated in FIG. 2 toward the upper side (inner side of the sample 20) of the sample 20). An enwedge of the defect D within the sample 20 is referred to as a tip of the defect D.

It is assumed that an ultrasonic wave that propagates in the sample 20 reaches the aperture A of the defect D. The ultrasonic wave is reflected in the vicinity of a corner (or in the vicinity of the aperture) twice in general, except for special cases. The ultrasonic wave is strongly reflected in a direction opposite to a direction in which the ultrasonic wave has propagated. Then, the ultrasonic wave is received. The ultrasonic wave is referred to as a corner echo.

The corner echo, however, propagates in a wide range in addition to the direction in which the received wave has propagated. This can be qualitatively understood from the following fact. As illustrated in FIG. 2, a part that is located in the vicinity of the aperture A of the defect D is displaced by the ultrasonic wave in the same direction of the propagation direction. The displaced aperture of the defect becomes a minute oscillation source. If the ultrasonic wave propagates from the oscillation source, the ultrasonic wave reflected on the aperture A of the defect D propagates in the wide range.

Next, a wave that is diffracted from the tip of the defect is described.

Figure 3A:
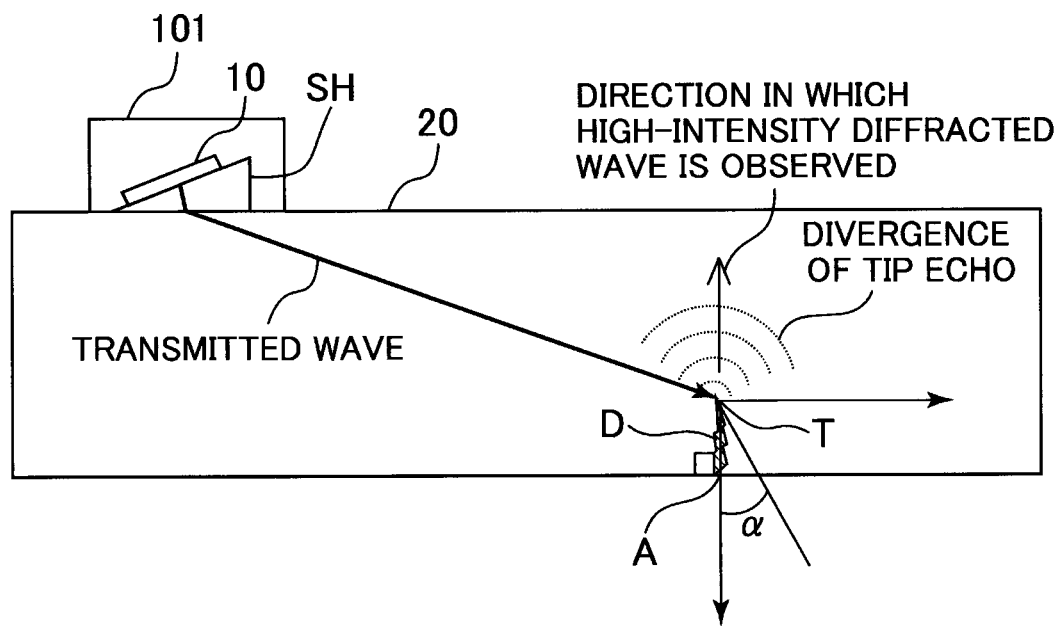
FIGS. 3A and 3B are diagrams illustrating a wave diffracted from a tip of a defect.
Figure 3B:
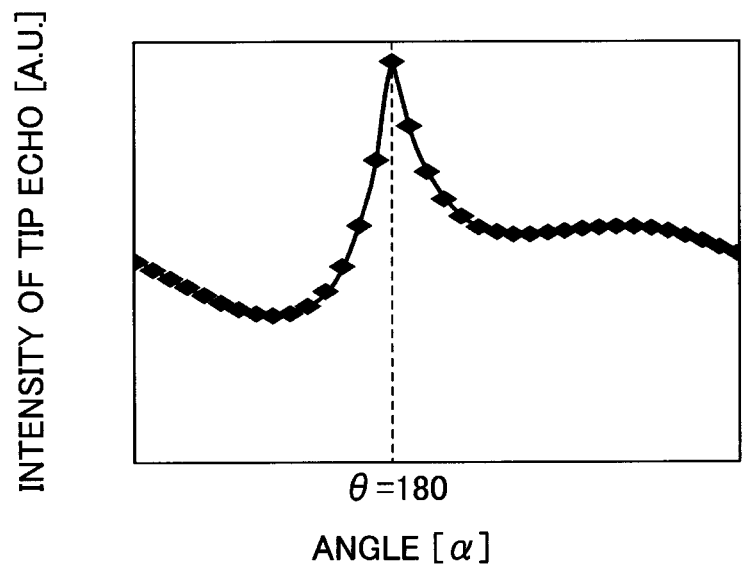

FIGS. 3A and 3B are diagrams illustrating the wave diffracted from the tip of the defect.

As illustrated in FIG. 3A, an ultrasonic probe 101 includes an ultrasonic oscillation element 10 and a wedge SH. The wedge SH is of a wedge shape. The ultrasonic oscillation element 10 is arranged on an upper surface of the wedge SH. The wedge SH causes a lower surface of the ultrasonic oscillation element 10 to be inclined with respect to an upper surface of the sample 20. The ultrasonic wave that is output from the ultrasonic oscillation element 10 is refracted on the upper surface of the sample 20 and incident on the sample 20 at an oblique angle.

The ultrasonic wave transmitted by the ultrasonic oscillation element 10 reaches the tip T of the defect D, where a wave is diffracted. The diffracted wave spreads in all directions from the tip T, propagates and is received. The diffracted wave is referred to as a tip echo. FIG. 3B illustrates an intensity distribution of the wave diffracted when the ultrasonic wave is incident on the tip T from a direction oblique to the direction of the extension of the defect D. As illustrated in FIG. 3B, the diffracted wave relatively strongly propagates in the direction in which the defect D develops. An angle θ indicated in FIG. 3B indicates an angle with respect to a standard direction that is a downward direction from the aperture A of the defect D. As illustrated in FIG. 3B, the diffracted wave strongly propagates at an angle θ of 180 degrees or in the direction in which the defect D develops.

Next, a principle of an ultrasonic test method executed by the ultrasonic inspection apparatus according to the present embodiment is described with reference to FIG. 4.

Figure 4:
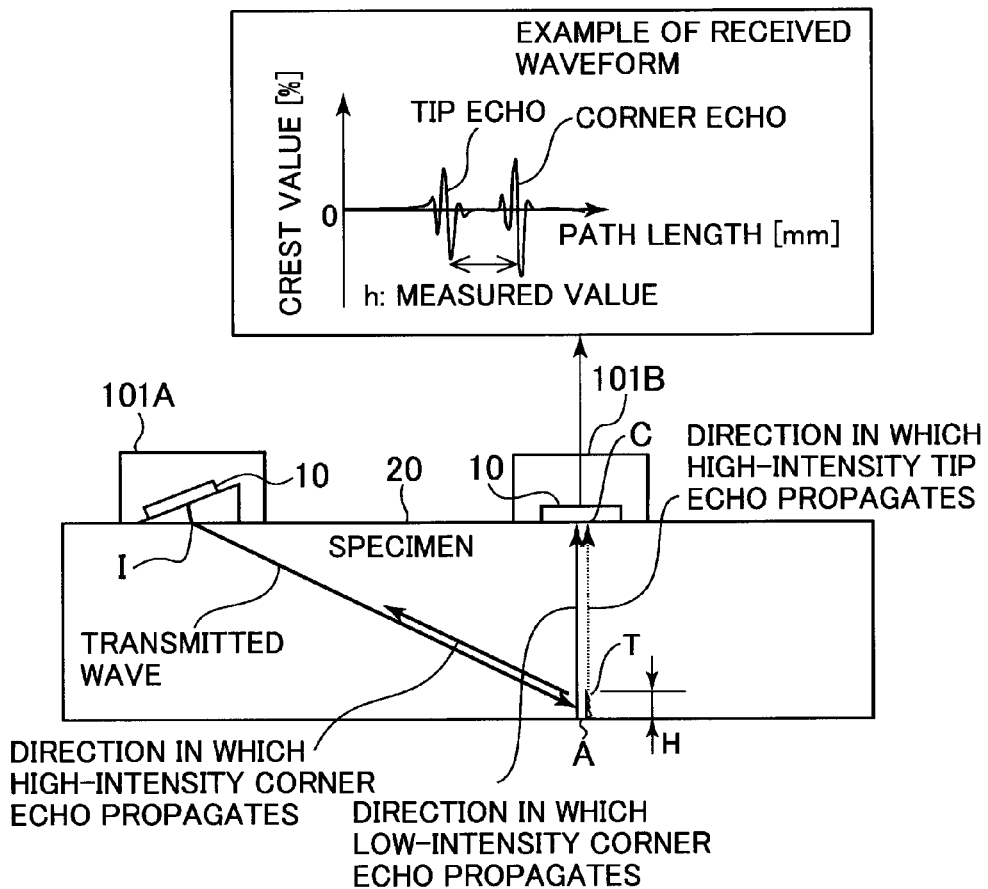
FIG. 4 is a diagram illustrating a principle of an ultrasonic test method executed by an ultrasonic inspection apparatus according to an embodiment of the invention.

FIG. 4 is a diagram illustrating the principle of the ultrasonic test method executed by the ultrasonic inspection apparatus according to the embodiment of the invention.

In the present embodiment, a transmitting probe 101A and a receiving probe 101B are used. The transmitting probe 101A includes the ultrasonic oscillation element 10 and the wedge SH as illustrated in FIG. 3A. The receiving probe 101B includes an ultrasonic oscillation element 10.

As the transmitting probe 101A, a probe that is capable of executing an angle beam method in the same manner as the SPOD method and the delta method is used. The transmitting probe 101A is arranged at a position (incidence point I) at which the angle beam method is executed on the defect D. As the receiving probe 101B, a probe that is capable of executing a vertical beam method is used. The receiving probe 101B is arranged at a position (reception point C) at which the vertical beam method is executed on the defect D.

An ultrasonic wave is transmitted by the angle probe (transmitting probe 101A) and incident on the defect D in a direction oblique to a direction in which the defect D develops, and a wave is diffracted from the tip T of the defect D.

The receiving probe 101B receives the diffracted wave directly propagating upward from the tip T of the defect D and the ultrasonic wave reflected from the corner (aperture A of the defect D) and propagating upward due to divergence of the ultrasonic wave. The ultrasonic inspection apparatus evaluates the height H of the defect D from a back surface of the tip T on the basis of the difference h between a propagation time of the diffracted wave and a propagation time of the reflected wave. The difference h between the propagation times that corresponds to the height H of the defect D occurs.

Next, a principle of measuring the height of the defect by the ultrasonic inspection apparatus according to the present embodiment is described with reference to FIGS. 5 to 8.

FIGS. 5 to 8 are diagrams illustrating the principle of measuring the height of the defect by the ultrasonic inspection apparatus according to the embodiment of the invention.

Figure 5:
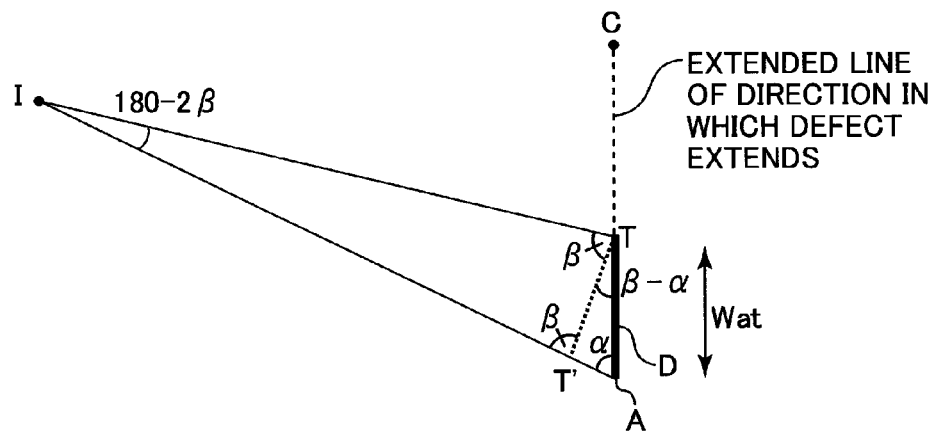
FIG. 5 is a diagram illustrating a principle of measuring the height of a defect by the ultrasonic inspection apparatus according to the embodiment of the invention.

In FIG. 5, a point at which the ultrasonic wave illustrated in FIG. 1 is incident is indicated by I, and a point at which the ultrasonic wave is received is indicated by C. In FIG. 5, the aperture of the defect D is indicated by A, and the tip of the defect D is indicated by T. The height of the defect D is a distance between the aperture A of the defect D and the tip T, with the tip of the defect D being indicated by Wat. A distance between the aperture A of the defect D and the reception point C is indicated by Wac. A distance between the tip T of the defect D and the reception point C is indicated by Wtc.

The actual height Wat of the defect D is a value of (Wac−Wtc) as understood from FIG. 5. In the ultrasonic test method, however, a waveform of the wave that is received at the reception point C is evaluated. If the height of the defect is simply evaluated from the difference between the length of a path in which the corner echo appears and the length of a path in which the tip echo appears, a measured value h (illustrated in FIG. 4) is expressed by the following Equation (2).

$$h = (Wia + Wac) - (Wit + Wtc) \quad (2)$$

A distance Wia between the incidence point I and the aperture A of the defect D is different by a distance Wt'a between the aperture A and a point T' from a distance Wit between the incidence point I and the tip T of the defect D. In order to obtain the actual height, the distance Wt'a needs to be subtracted from the measured value h. The height Wat of the defect D is expressed by the following Equation (3).

$$Wat = Wac - Wtc = h - Wt'a \quad (3)$$

When the distance Wia is a known value from the measured value, the distance Wt'a is expressed by the following Equation (4) on the basis of a geometric relationship.

$$Wt'a = Wia - Wit \quad (4)$$

If the defect is minute, it is difficult to separate the tip echo from the corner echo and distinguish between the tip echo and the corner echo in a normal angle beam method. In this case, an angle β can be approximated to 90 degrees in a geometric relationship. In order that the measured value h has a value close to the actual height of the defect, a value hs obtained by correcting the measured value h can be expressed by the following Equation (5).

$$hs = h/(1 + \cos \alpha) \quad (5)$$

In Equation (5), an angle α is an angle between the direction in which the defect D develops and the direction in which the ultrasonic wave is transmitted. If the defect is minute, a value required for the correction is small. Thus, to avoid undervaluing the defect, the measured value h may be used without correction.

On the other hand, if the defect is sufficiently larger than the divergence of the transmitted ultrasonic wave, the corner echo and the tip echo may not be simultaneously displayed on a received waveform. In this case, the angle β cannot be approximated to 90 degrees. Thus, a case where a single probe is used and a case where an array probe is used are separately considered.

Figure 6:
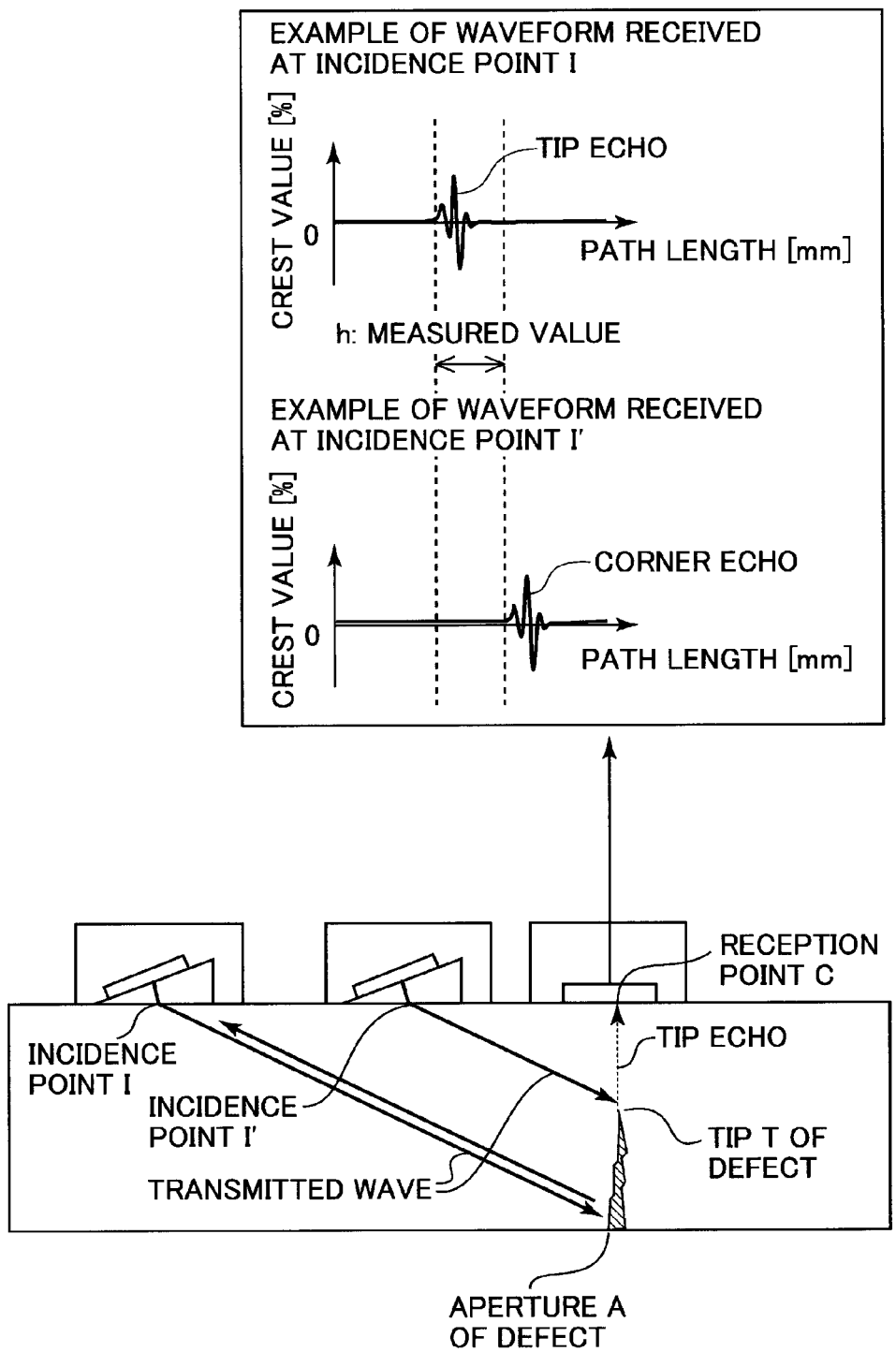
FIG. 6 is a diagram illustrating a principle of measuring the height of a defect by the ultrasonic inspection apparatus according to the embodiment of the invention.
Figure 7:
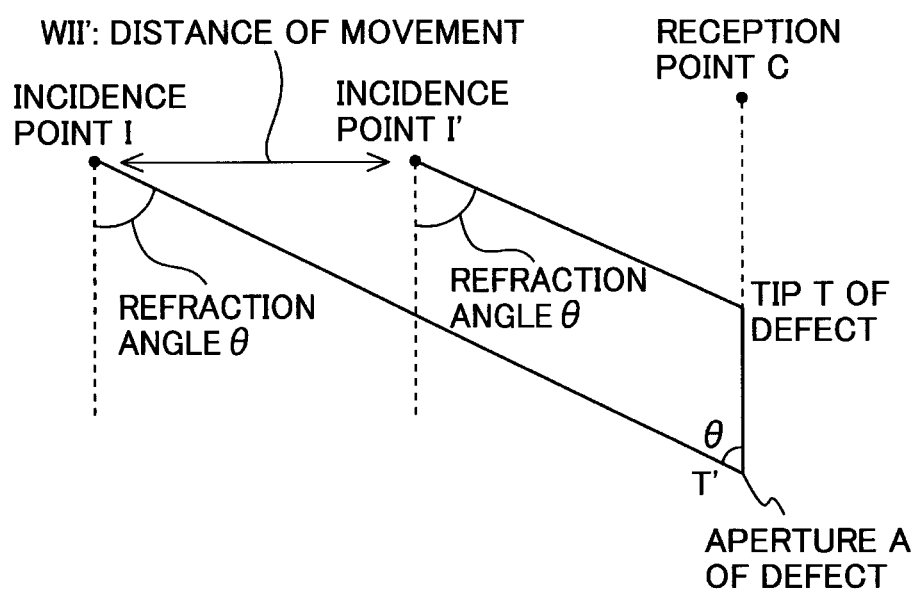
FIG. 7 is a diagram illustrating a principle of measuring the height of a defect by the ultrasonic inspection apparatus according to the embodiment of the invention.

FIG. 6 illustrates the case where a single probe is used as the transmitting probe and the defect to be measured is large.

If the single probe is used as the transmitting probe, the probe needs to move in the same manner as procedures of the angle beam method. In this case, the probe moves to an incidence point I' that causes the tip echo to have the maximum intensity. Positional relationships among the incidence points I and I', the aperture A of the defect, the tip T of the defect and the reception point C are relationships illustrated in FIG. 7. When the height of the defect is evaluated using the method described with reference to FIG. 4 and a distance of the movement of the transmitting probe is indicated by Wii', the following Equation (6) is established.

$$hs = h - (Wii'/\sin \theta) \quad (6)$$

Figure 8:
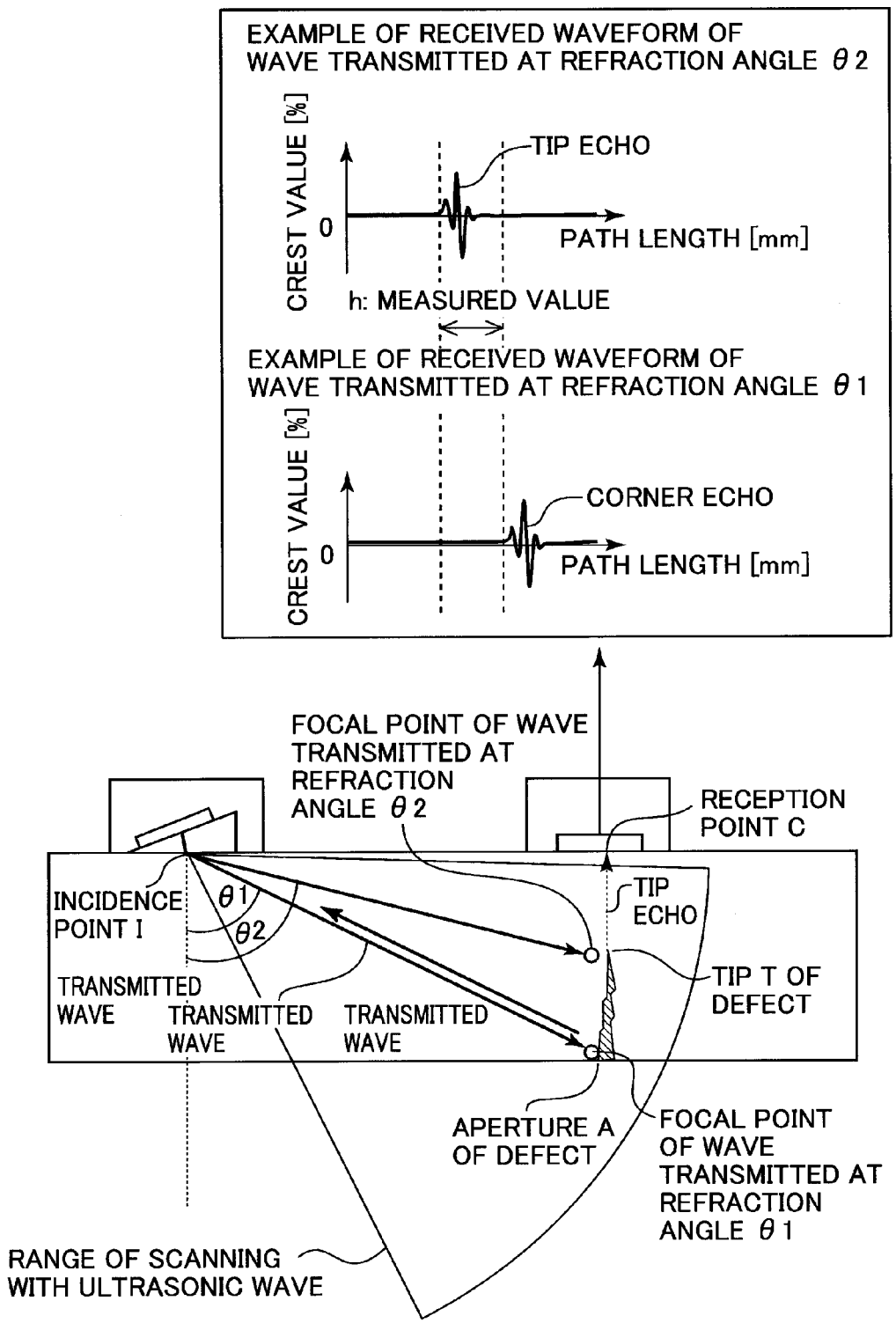
FIG. 8 is a diagram illustrating a principle of measuring the height of a defect by the ultrasonic inspection apparatus according to the embodiment of the invention.

FIG. 8 illustrates the case where the array probe is used as the transmitting probe and the defect to be measured is large.

If the array probe is used, the probe can cause the ultrasonic wave to be refracted at a desired angle and focused and electronically scan the defect with the ultrasonic wave. Waveform data obtained when the array probe is used is waveform data obtained from the positional relationships in which the incidence point I is fixed as illustrated in FIG. 5. In this case, only the corner echo is detected from the ultrasonic wave transmitted at a refraction angle θ1 and propagating in a path extending from the incidence point I through the aperture A to the reception point C, and only the tip echo is detected from the ultrasonic wave transmitted at a refraction angle θ2 and propagating in a path extending from the incidence point I through the tip T to the reception point C. The following Equation (7) is established using the refraction angles θ1 and θ2 that cause the corner echo and the tip echo to have the maximum intensities.

$$hs = h/(1 + (\cos((\theta 1 + \theta 2)/2)/\cos((\theta 2 - \theta 1)/2))) \quad (7)$$

When the defect is inspected by an inspection method (described later with reference to FIGS. 9 and 12) and an angle beam method using a transmitting probe that transmits and receives an ultrasonic wave, a distance between the incidence point and the tip T is measured by the transmission and reception of the ultrasonic wave by the array probe and can be expressed by the following Equation (8).

$$hs = h - (Wia - Wit) \quad (8)$$

Next, the configuration of the ultrasonic inspection apparatus according to the present embodiment is described with reference to FIGS. 9 to 11.

Figure 9:
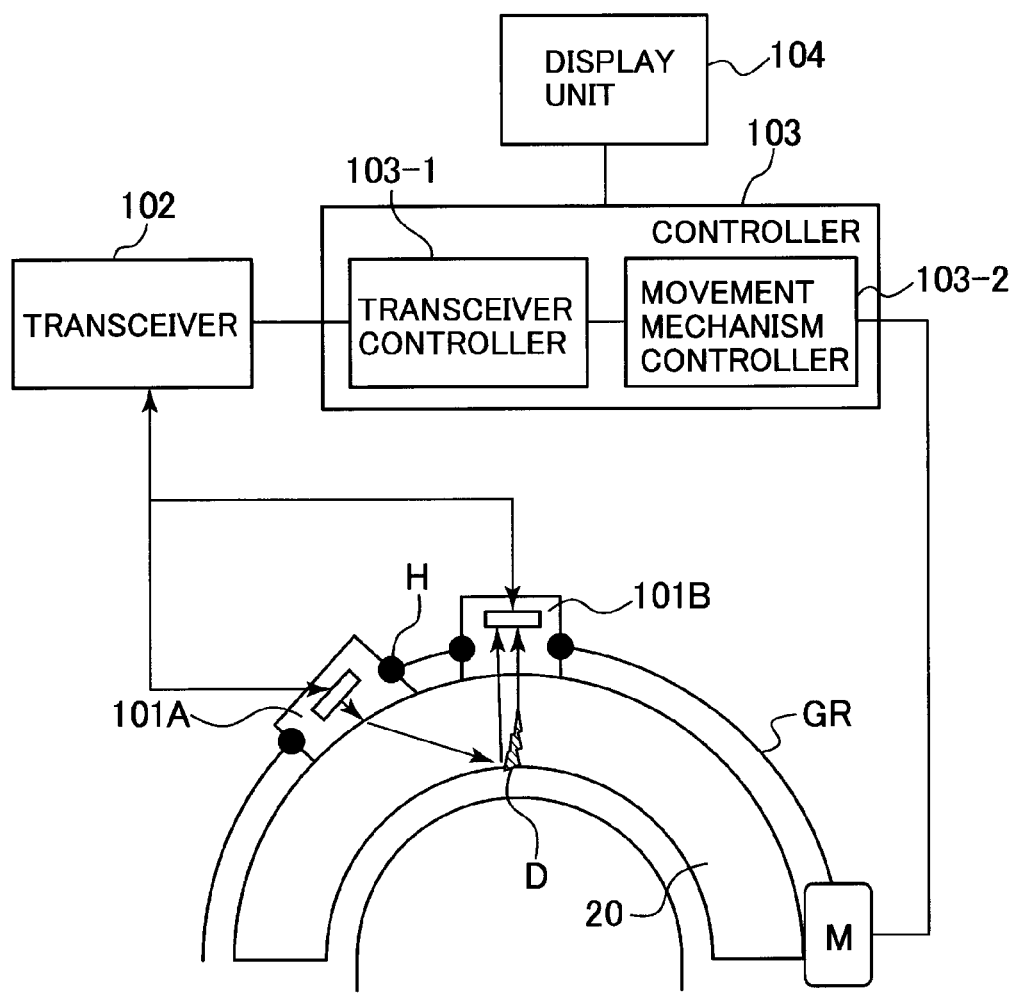
FIG. 9 is a diagram illustrating an outline configuration of the ultrasonic inspection apparatus according to the embodiment of the invention when the ultrasonic inspection apparatus executes an inspection.
Figure 10:
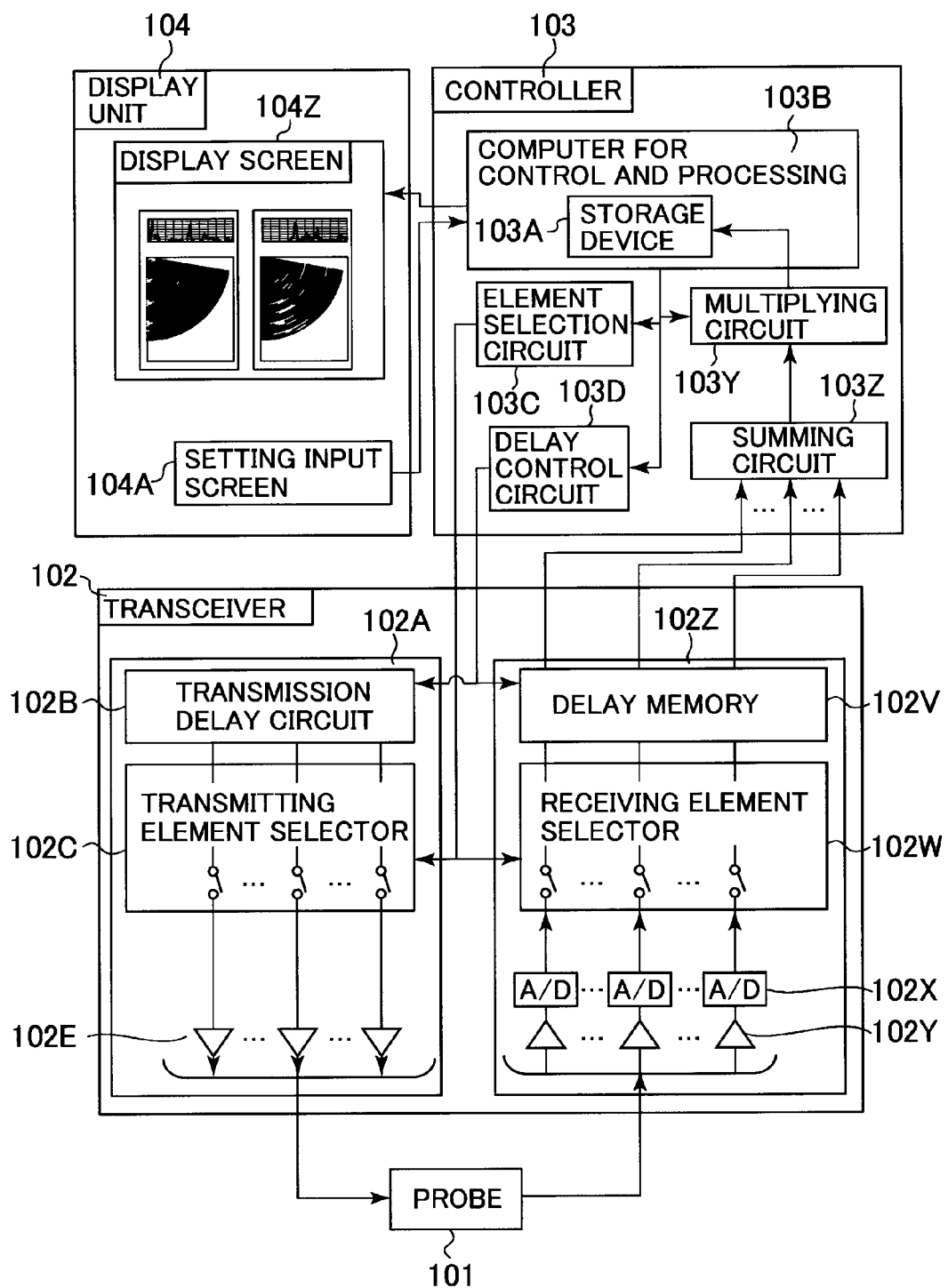
FIG. 10 is a block diagram illustrating the configuration of the ultrasonic inspection apparatus according to the embodiment of the invention.

FIG. 9 is a diagram illustrating an outline configuration of the ultrasonic inspection apparatus according to the embodiment of the invention when the ultrasonic inspection apparatus executes an inspection. FIG. 10 is a block diagram illustrating the configuration of the ultrasonic inspection apparatus according to the embodiment of the invention. FIG. 11 is a diagram illustrating setting of the array probe included in the ultrasonic inspection apparatus according to the embodiment of the invention.

FIG. 9 illustrates an example of the whole configuration of the ultrasonic inspection apparatus and an example of the inspection of a pipe. The pipe or sample 20 is provided with a guide rail GR on the outer circumference thereof. The transmitting probe 101A and the receiving probe 101B are held by a holder H and attached to the guide rail GR so that the probes 101A and 101B can move. The transmitting probe 101A is capable of executing the angle beam method, while the receiving probe 101B is capable of executing the vertical beam method. The guide rail GR and a motor M form a movement mechanism. The guide rail GR is rotationally moved by the motor M along the outer circumference of the sample 20. Thus, the transmitting probe 101A and the receiving probe 101B can move on the outer circumference of the sample 20.

The ultrasonic inspection apparatus according to the embodiment includes the transmitting probe 101A, the receiving probe 101B, a transceiver 102, a controller 103 and a display unit 104.

The transceiver 102 controls transmission and reception of an ultrasonic wave by the transmitting probe 101A and controls reception of an ultrasonic wave by the receiving probe 101B so that a defect detection mode and a sizing mode can be achieved. In the defect detection mode, the probe 101A that is capable of executing the angle beam method transmits and receives an ultrasonic wave so as to detect a defect in the angle beam method. In the sizing mode, the probe 101A that is capable of executing the angle beam method transmits an ultrasonic wave, the probe 101B that is capable of executing the vertical beam method receives the ultrasonic wave, and the ultrasonic inspection apparatus measures the height of a minute defect. When the defect detection mode is applied, the probe 101A is used for transmission and reception of an ultrasonic wave. The controller 103 includes a transceiver controller 103-1 and a movement mechanism controller 103-2. The transceiver controller 103-1 controls transmission and reception of an ultrasonic wave by the transceiver 102. The movement mechanism controller 103-2 controls the movement mechanism. Data obtained by the ultrasonic test method is displayed on and stored in the display unit and evaluated on the display unit. If the shape of the sample is unclear, the movement mechanism may move the two probes to desired positions.

Next, the detailed configuration of the ultrasonic inspection apparatus according to the embodiment is described with reference to FIG. 10. The ultrasonic inspection apparatus according to the embodiment can achieve the defect detection mode and the sizing mode. In the defect detection mode, the transmitting probe that is capable of executing the angle beam method transmits and receives an ultrasonic wave at an oblique angle so as to detect a defect in the angle beam method. In the sizing mode, the transmitting probe transmits an ultrasonic wave, the receiving probe receives the ultrasonic wave, and the ultrasonic inspection apparatus measures the height of a minute defect. Before data obtained by the two methods is displayed, a gain adjustment can be executed in response to the modes, and results of the ultrasonic test method can be displayed. In this case, an array probe is used as a transmitting and receiving probe.

The transceiver 102 includes a pulsar 102A and a receiver 102Z. The pulsar 102A provides a delay time to the array probe 101 and causes the array probe 101 to transmit an ultrasonic wave. The receiver 102Z receives an ultrasonic wave, and converts the received ultrasonic wave into a digital signal that is treated as a received signal. The controller 103 includes an element selection circuit 103C, a delay control circuit 103D, a summing circuit 103Z, a multiplying circuit 103Y, a storage device 103A and a computer 103B for control and processing. The element selection circuit 103C switches ultrasonic oscillation elements and controls the ultrasonic oscillation elements when necessary. The ultrasonic oscillation elements are used for elements for transmitting and receiving ultrasonic waves. The delay control circuit 103D controls delays for transmission and reception. The summing circuit 103Z sums received signals. The multiplying circuit 103Y multiplies the summed signal by a gain in accordance with an ultrasonic test mode. The storage device 103A stores a pattern for controlling the parts of the controller 103 and the received signals. The computer 103B executes a process according to the pattern for controlling. The display unit 104 has a setting input screen 104A and a display screen 1042. Various settings are displayed on the setting input screen 104A. Signals received by the ultrasonic test method and a measured image can be displayed on the display screen 104Z.

Next, operations are described. First, the computer 103B transmits a transmitter/receiver switching signal to the element control circuit 103C before an ultrasonic wave is transmitted and received and a signal reflected from a target to be measured is stored. The transmitter/receiver switching signal is used to select ultrasonic oscillation elements to be used for transmission and reception of ultrasonic waves. The computer 103B provides delay times through the delay control circuit 103D to the ultrasonic oscillation elements for focusing, transmitting and receiving ultrasonic waves. A transmission delay circuit 102B, which has received transmission signals and the delay times, delays the transmission signals by the received delay times and transmits the transmission signals to a transmitting element selector 102C. The transmitting element selector 102C receives the transmission signals delayed by the delay times by the transmission delay circuit 102B, selects the transmitting elements on the basis of a signal (for selecting the transmitting elements) transmitted by the element control circuit 103C, and transmits the transmission signals to transmission amplifiers 102E. The transmission amplifiers 102E amplify the transmission signals and apply driving voltages for transmission of ultrasonic waves to the elements included in the probe 101. In this case, the transmitting element selector 102C is capable of simultaneously transmitting the transmission signals to each of elements included in the probe 101B or a plurality of elements included in the probe 101B. The elements that have received the amplified transmission signals transmit ultrasonic waves using a piezoelectric effect. As described above, when the transmission signals are delayed by delay times and the voltages are applied to the elements of the probe 101, the elements delay the ultrasonic waves by the delay times and then transmit the ultrasonic waves. In order to focus the ultrasonic waves, the voltages are applied to the ultrasonic oscillation elements after being delayed by times corresponding to geometric distances between the ultrasonic oscillation elements and a point on which the ultrasonic waves are focused or corresponding to distances based on speeds of the ultrasonic waves propagating in media and refraction at an interface, and the ultrasonic oscillation elements transmit the ultrasonic waves while focusing the ultrasonic waves on a predetermined position within a sample.

The receiver 102Z receives the ultrasonic waves returning from the sample. In order to process electric signals generated by a piezoelectric effect, reception amplifiers 102Y amplify received signals in response to the ultrasonic waves received by the elements of the probe 101, and analog-to-digital converters 102X converts the received analog signals into digital signals. In addition, a receiving element selector 102W selects receiving elements and receives signals from the selected receiving elements. The selected received digital signals are stored in a delay memory 102V. In this case, when the ultrasonic waves are focused and received, delays that are transmitted from the delay control circuit 103D are given to the signals received by the ultrasonic oscillation elements in a similar manner as the transmission of the ultrasonic waves and are stored. A waveform obtained by summing the signals by the summing circuit 103Z includes a waveform obtained in the defect detection mode by the angle beam method and a waveform obtained in the sizing mode. Thus, the waveforms are corrected using correction gains G1 and G2 (described with reference to FIG. 11) by the multiplying circuit 103Y and transmitted to the computer 103A for control and processing so that intensities of the waveforms can be appropriate and images of the waveforms can be displayed.

In order to simply set a combination of ultrasonic oscillation elements to be used for transmission and reception, information about combinations of elements that are to be used for transmission and reception and are included in the probes is stored in the storage device 103A of the computer 103 for control and processing. A combination of ultrasonic oscillation elements to be used for transmission and reception is specified. Before the start of a measurement, information about the specified combination is read. The transmitting element selector 102C operates for the transmission. The receiving element selector 102W operates for the reception.

An example of a data table that includes information of combinations of elements to be used for transmission and reception and delay times is described with reference to FIG. 11.

A combination, suitable for a focal point F(i), of ultrasonic oscillation elements to be used for transmission is selected and reflected in the transmitting element selector 102C. Another combination, suitable for the focal point F(i), of ultrasonic oscillation elements to be used for reception is selected and reflected in the receiving element selector 102W. Thus, the ultrasonic oscillation elements to be used for transmission and reception are limited. FIG. 11 illustrates the example of the data table that is displayed and indicates that ON=(positive delay: Pik, Pik) and OFF=−1. The aforementioned description assumes the array probe. For example, a case where M=1 and N=1 corresponds to a case where a single probe is used. A case where delay times T1, 1=0, R1, 1=0, T2, 1=0 and R2, 2=0 corresponds to a case where a single probe is used for transmission and reception. If a delay time is "−1", the delay time indicates that an ultrasonic wave is not transmitted or received.

Details of an inspection method to be executed by the ultrasonic inspection apparatus according to the present embodiment are described with reference to FIG. 12.

Figure 12:
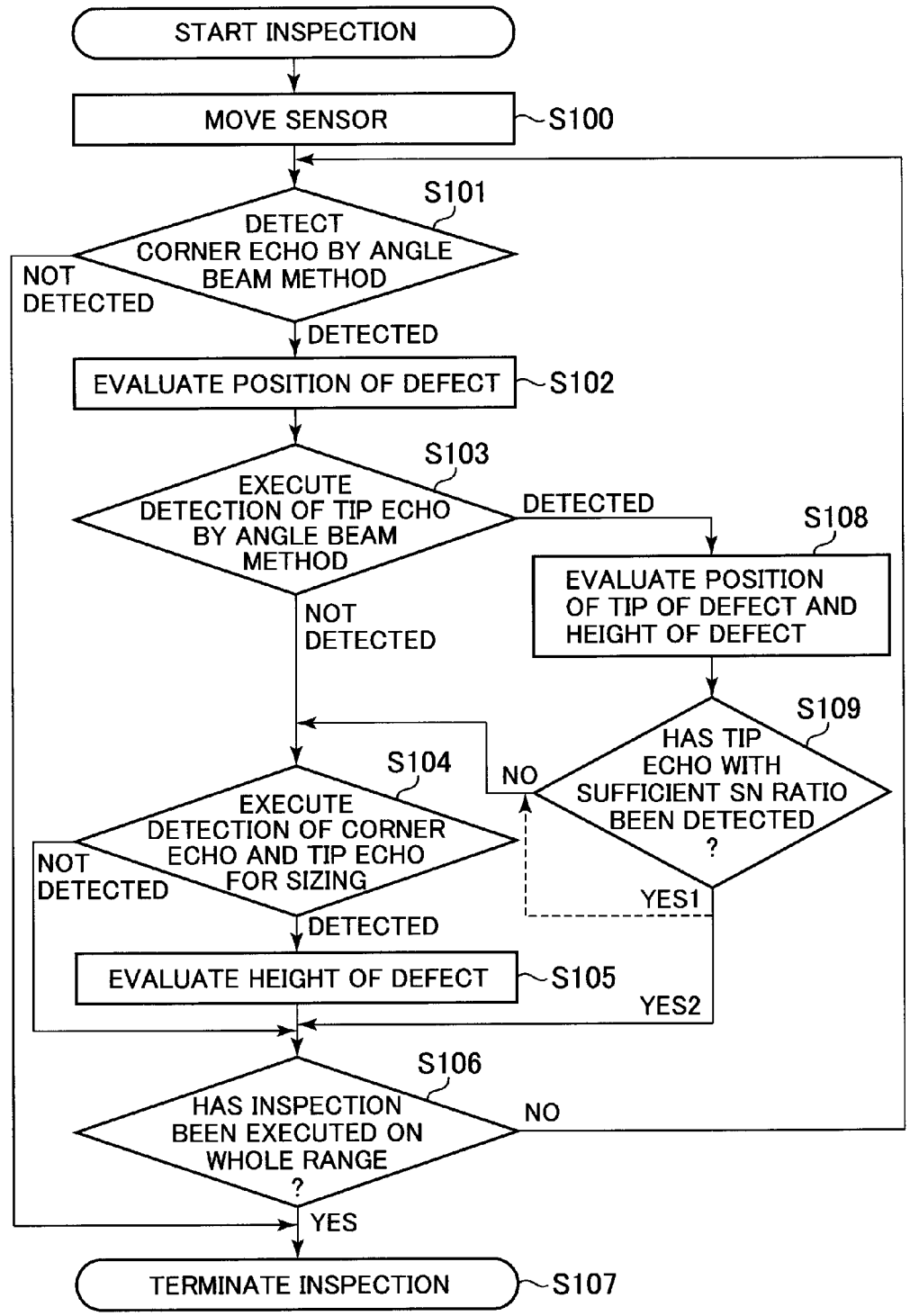
FIG. 12 is a flowchart of details of an inspection method to be executed by the ultrasonic inspection apparatus according to the embodiment of the invention.

FIG. 12 is a flowchart of the details of the inspection method to be executed by the ultrasonic inspection apparatus according to the embodiment of the invention.

As described with reference to FIG. 9, the probe 101 is placed on the sample 20, and the inspection starts.

In step S100, the probe 101 is moved by the movement mechanism.

In step S101, only the transmitting probe 101A is used, detects a corner echo using the angle beam method, and thereby determines whether or not a defect exists. In this case, the probe 101A transmits an ultrasonic wave and receives a wave reflected from the defect or the like, with the probe 101A being used for the transmission and the reception. If the corner echo is not detected from a range to be inspected, the process proceeds to step S107 and is terminated.

On the other hand, if the corner echo is detected, the computer 103B for control and processing evaluates the position of the defect based on a path length displayed with a received waveform and a refraction angle.

If the corner echo is detected, a tip echo is searched by the angle beam method in step S103. Normally, an angle at which a single angle probe transmits an ultrasonic wave is fixed. Thus, if the defect is minute, the corner echo and the tip echo are simultaneously displayed, like the example of the received waveform illustrated in FIG. 4. If the defect is large, the corner echo and the tip echo are not simultaneously displayed in some cases.

If the tip echo is not detected, the defect is considered to be minute. Thus, in step S104, the receiving probe 101B is placed immediately above the defect on the basis of the position (of the defect) obtained by a waveform of the tip echo detected in step S103, and the corner echo and the tip echo are searched by the method described with reference to FIG. 4. If the tip echo cannot be detected by the method with reference to FIG. 4, the defect is determined to be a reflector that is not worthy of evaluation. In step S106, it is determined whether a whole range to be inspected has been completely inspected.

If the corner echo and the tip echo are detected in step S104, sizing is executed on the basis of the difference between path lengths of the echoes in step S105. In order to accurately execute the sizing, the aforementioned Equation (5) is used as an equation for correcting the height of the defect if the defect is minute. If the defect is large, Equation (7) or (8) is used.

In step S106, it is determined whether or not the inspection has been executed on the whole range. If the inspection has not been executed on the whole range, the process returns to step S101. If the inspection has been executed on the whole range, the inspection is terminated in step S107.

In this case, the tip echo can be detected by a normal angle beam method. In such a case, the height of the defect can be evaluated using a conventional method. The intensity of the tip echo, however, is low. Thus, it is risky to evaluate the height of the defect when the detected tip echo does not have a sufficient intensity. A threshold for an SN ratio of the tip echo is provided. When the SN ratio is equal to or lower than the threshold, the height of the defect is supplementarily evaluated using the method described with referenced to FIG. 4. Even when the SN ratio is sufficient and the tip echo is detected, it is effective to supplementarily hold data. Thus, if the tip echo can be detected in step S103, the sizing is executed using the angle beam method that is generally used in step S108.

In step S109, it is determined whether or not the SN ratio of the detected tip echo is sufficient in order to execute the sizing. If the SN ratio of the detected tip echo is not sufficient, the sizing is executed using the method described with reference to FIG. 4 in step S104. In order to accurately execute the sizing, Equation (5), (7) or (8) is used depending on whether the single probe or the array probe is used. If the defect has a size that causes the SN ratio of the detected tip echo to be sufficient, the evaluation of the defect may be terminated and the process may proceed to step S106. Alternatively, the process may proceed to step S104 and data obtained by the sizing using the method described with reference to FIG. 4 may be held.

Next, details of another inspection method to be executed by the ultrasonic inspection apparatus according to the present embodiment are described with reference to FIG. 13.

Figure 13:
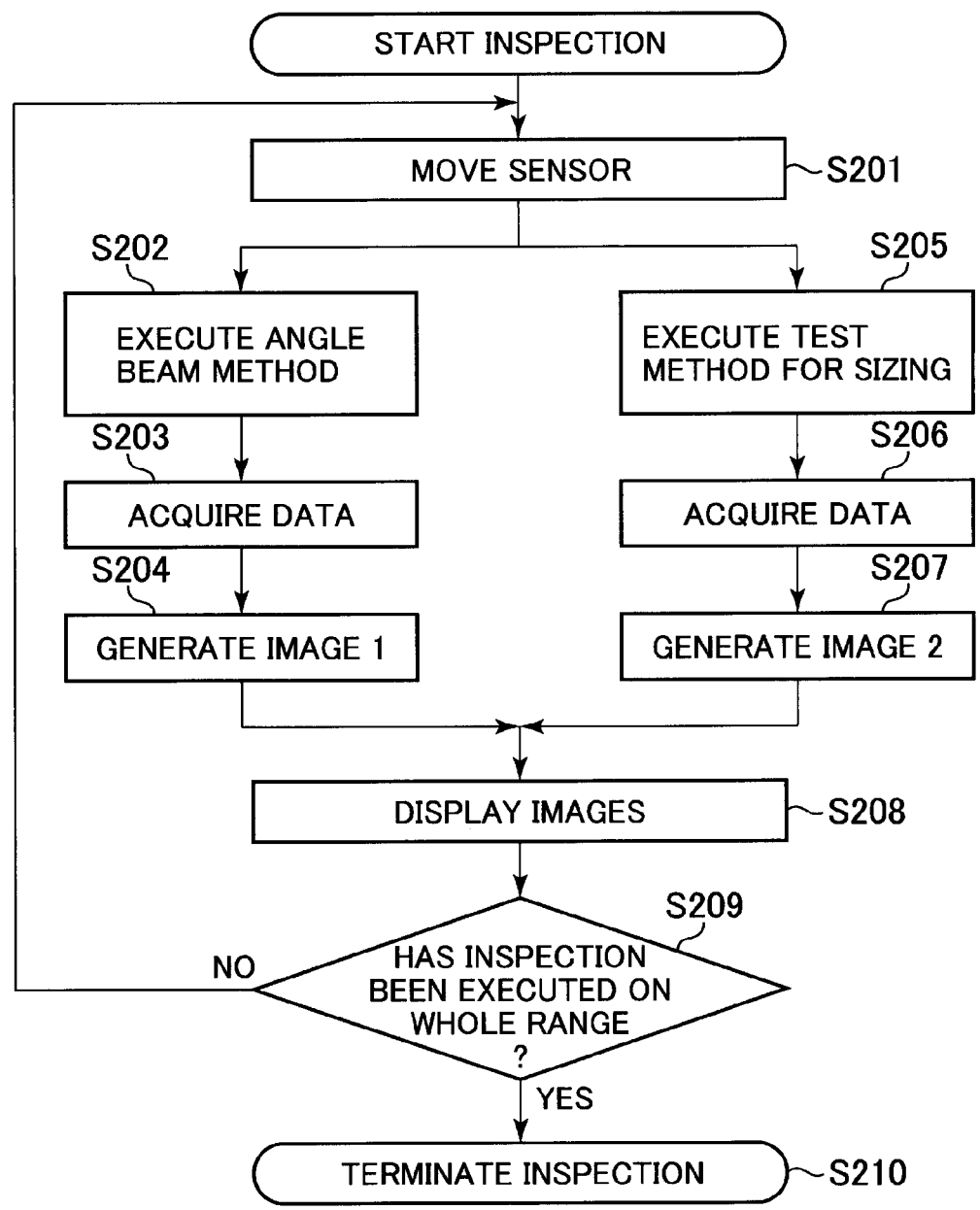
FIG. 13 is a flowchart of details of another inspection method to be executed by the ultrasonic inspection apparatus according to the embodiment of the invention.

FIG. 13 is a flowchart of the details of the other inspection method to be executed by the ultrasonic inspection apparatus according to the embodiment of the invention.

The inspection method that is executed when the sample has a constant thickness is described below.

Samples to be subjected to a non-destructive inspection using an ultrasonic wave are represented by pipes, flat steel plates or the like. In many cases the shape of such samples and the type of a defect to be inspected are limited. If the thickness of the sample is constant and it is expected that a defect develops in the direction of a normal to a back surface of the sample or in a direction nearly parallel to the direction of the normal, the positional relationship between the two probes 101A and 101B can be fixed. Therefore, the probes are moved while keeping the fixed positional relationship between the two probes and the inspection is executed using the method described with reference to FIG. 4.

More specifically, the probes 101A and 101B are placed on the sample 20 and the inspection is started.

In step S201, the probes 101A and 101B is moved while the positional relationship between the probes 101A and 101B is fixed.

In step S202, a defect on the sample is detected by the angle beam method. In step S203, data on the defect is acquired. In step S204, the acquired data is imaged.

In step S205, a corner echo and a tip echo are detected from the defect of the sample using the method described with reference to FIG. 4. In step S206, data of the defect is acquired. In step S207, an image of the acquired data is generated.

In step S208, the two images are displayed.

In step S209, it is determined whether the inspection has been executed on a whole target range. If the inspection has been executed on the whole target range, the inspection is terminated in step S210. If the inspection has not been executed on the whole target range, the process returns to step S201.

Next, a method for displaying images by the ultrasonic inspection apparatus according to the present embodiment is described with reference to FIGS. 14A to 15B.

FIGS. 14A to 15B are diagrams describing the method for displaying images by the ultrasonic inspection apparatus according to the embodiment of the invention.

In the method for displaying images, a single probe or an array probe is used as the transmitting probe, and a single probe or an array probe is used as the receiving probe. Four combinations of the probes are available. If the single probe is used as the transmitting probe, the probes execute the ultrasonic test method at specific locations, and data that can be displayed is two waveforms obtained by the angle beam method and the method described with reference to FIG. 4. If the array probe is used as the transmitting probe, the probes execute the ultrasonic test method at specific locations, and data that can be displayed is two-dimensional images obtained by the angle beam method and the method described with reference to FIG. 4. In the angle beam method, the images can be obtained by linear scanning or sector scanning and displayed. In the method described with reference to FIG. 4, the two-dimensional images can be displayed by displaying data on the basis of a pattern of linear scanning or a refraction angle of sector scanning.

Figure 14A:
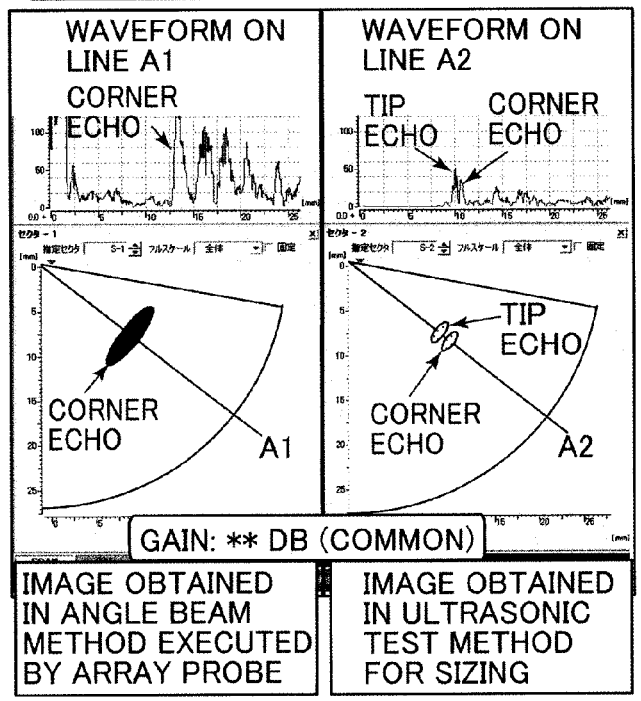
FIGS. 14A and 14B are diagrams describing a method for displaying images by the ultrasonic inspection apparatus according to the embodiment of the invention.

FIG. 14A illustrates data obtained when the array probe is used as the transmitting probe, the single vertical probe is used as the receiving probe, the angle beam method is executed using sector scanning, and the ultrasonic test method is executed using the method described with reference to FIG. 4. In FIG. 14A, results of the sector scanning are illustrated on the left side and data obtained by the method described with reference to FIG. 4 is illustrated on the right side. The results of the sector scanning and the data obtained by the method described with reference to FIG. 4 are displayed on the basis of refraction angles determined by transmission patterns of the sector scanning. Data that can be displayed does almost not vary regardless of whether the single probe or the array probe is used as the receiving probe. Even if the receiving probe is changed from the single probe to the array probe or from the array probe to the single probe, only the depths of the focal points become variable or invariable or only sensitivities to the tip echo and the corner echo change.

Figure 14B:
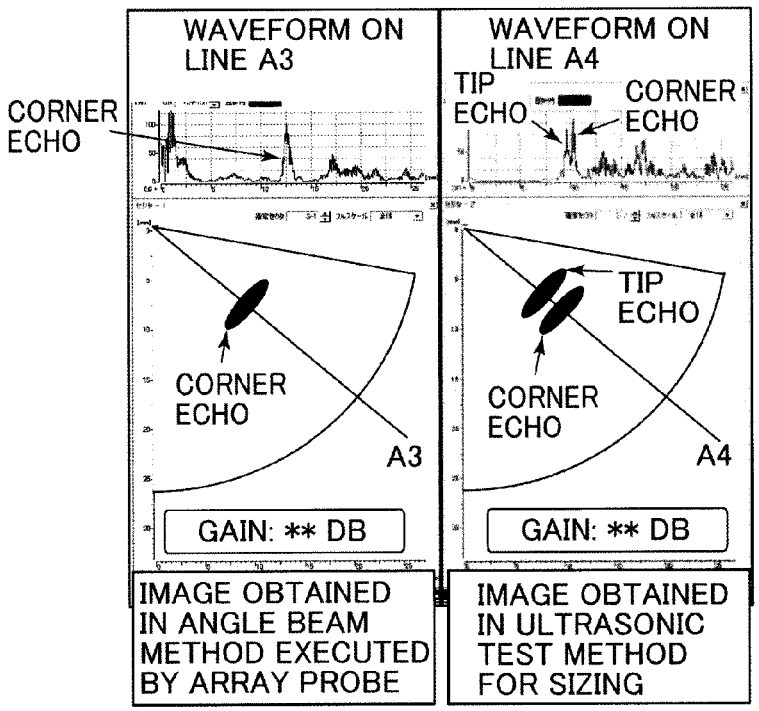

In general, the ultrasonic inspection is performed such that the intensity of a wave reflected from a reflector that is a standard is measured, and an ultrasonic sensitivity (gain) is preset based on the measured data, thereby using the gain to execute the ultrasonic test method. The inspection method according to the invention is obtained by combining the angle beam method and the method described with reference to FIG. 4. In the inspection method according to the invention, when the ultrasonic test method is executed using a constant gain, the following relationship results: the intensity of the corner echo obtained by the angle beam method>>the intensity of the corner echo obtained by the method described with reference to FIG. 4≈the intensity of the tip echo obtained by the method described with reference to FIG. 4. For example, when data obtained using an appropriate gain in the angle beam method is displayed, the intensity of a signal of an image obtained by the ultrasonic test method described with reference to FIG. 4 is low, and it is difficult for an inspector to recognize a diffracted wave. In order to overcome this problem, it is sufficient if gains can be separately adjusted for an image obtained by the angle beam method and an image obtained by the method according to the invention and the images can be displayed, as illustrated in FIG. 14B. The diffracted wave can be easily recognized by increasing the gain for the low-intensity signal of the image obtained by the ultrasonic test method described with reference to FIG. 4.

In the example illustrated in FIGS. 14A and 14B, an angle at which an ultrasonic wave is transmitted is treated as a polar coordinate θ, the transmitting probe causes the ultrasonic wave to be incident on the sample, and the receiving probe receives a waveform. A path length of the tip echo of the wave diffracted from the tip of the defect and a path length of the corner echo reflected from the corner are treated as polar coordinates r. The intensities of the received waveform are mapped at corresponding locations and displayed in a sector form.

Figure 15A:
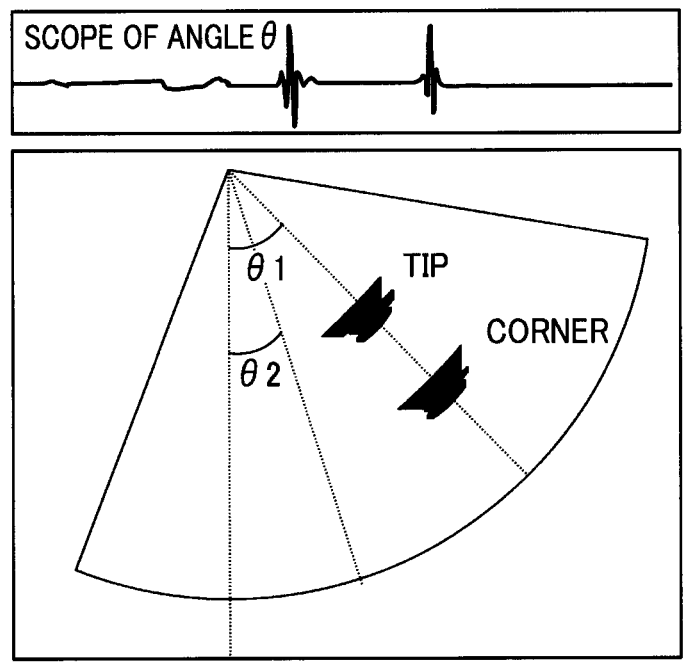
FIGS. 15A and 15B are diagrams describing a method for displaying images by the ultrasonic inspection apparatus according to the embodiment of the invention.
Figure 15B:
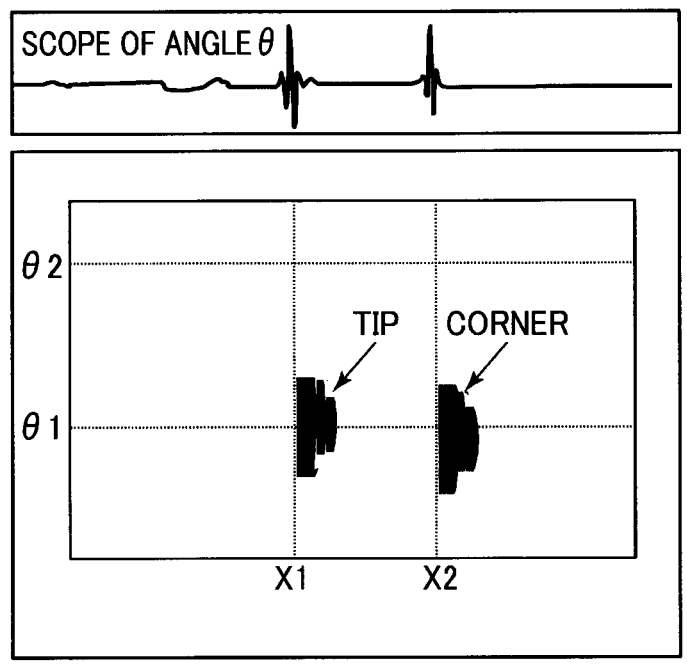

The received wave can be displayed as illustrated in FIG. 15B. FIG. 15A illustrates a display of the received wave using polar coordinates in the same manner as FIGS. 14A and 14B. In FIG. 15B, the ordinate indicates an angle at which the array probe transmits an ultrasonic wave. The transmitting probe causes the ultrasonic wave to be incident on the sample, and the receiving probe receives a waveform. In FIG. 15B, the abscissa indicates a path length of the tip echo of a wave diffracted from the tip of the defect and a path length of the corner echo reflected from the corner of the defect. The intensities of the received waveform are mapped and displayed as a two-dimensional image.

As described above, according to the embodiment, a corner echo that has a high intensity and is normally received at an oblique angle is received in a vertical direction in which the intensity of a sound wave is relatively low among a divergent sound wave, whereby the intensity of the corner echo can be reduced. On the other hand, the intensity of a diffracted wave distributed in a vertical direction is relatively high. Thus, the intensity of a signal of the wave diffracted from the tip of the defect can be relatively higher than the corner echo. As a result, it is possible to avoid the problem that the sizing cannot be executed due to absorption of the tip echo in the corner echo. Compared with the SPOD method, an ultrasonic wave that is transmitted by the transmitting probe is reflected on the bottom surface of the sample and is not directly received by the receiving probe. Thus, only the diffracted wave that propagates in the shortest path and reaches the receiving probe can be used without being affected by the shape of the sample. As a result, it is not necessary to evaluate a peak and path length of a diffracted wave weakened by an effect of reflection on a welded part or the bottom surface. For example, a sample with a large thickness can be inspected with a high sensitivity. In addition, a mode-converted wave is not used. Thus, a waveform of a wave propagating at a constant speed can be evaluated. As a result, it is easy to evaluate the waveform on the display unit displaying data on a defect to be inspected.

It is, therefore, possible to accurately and simply execute the sizing on a minute defect using an ultrasonic wave.

What is claimed is:

1. An ultrasonic inspection apparatus comprising;
   a holder that holds a transmitting probe capable of executing an angle beam method and a receiving probe capable of executing a vertical beam method;
   a movement mechanism that is capable of moving the transmitting probe and the receiving probe;
   a transceiver that executes an ultrasonic test mode in which the transmitting probe executes the angle beam method and thereby transmits and receives an ultrasonic wave and a sizing mode in which the transmitting probe transmits an ultrasonic wave and the receiving probe receives the ultrasonic wave;
   a controller that controls the transceiver and the movement mechanism; and
   a display unit that displays, stores and evaluates data obtained by the methods,
   wherein the transceiver includes
   a pulsar that includes a transmission delay unit for delaying a transmission signal corresponding to one or more elements included in the probe by a delay time and a transmitter for transmitting an ultrasonic wave, and
   a receiver that includes an analog-to-digital converter for converting the received ultrasonic wave to a digital signal and a memory unit for delaying the received signal by a delay time, and
   wherein the controller includes
   a delay controller that controls the delay times,
   a summing unit that sums received signals,
   a multiplier that multiplies a signal obtained by summing the received signals by the summing unit by a value set on the basis of the ultrasonic test mode, and
   a computer for control and processing that stores the received signals and has a processor for processing data.

2. The ultrasonic inspection apparatus according to claim 1,
   wherein an image obtained in the test mode and an image obtained in the sizing mode are separately adjusted using gains, and the gains are displayed on a screen.

3. The ultrasonic inspection apparatus according to claim 1, further comprising
   a sound-absorbent material that fixes the position of the transmitting probe and the position of the receiving probe and is arranged between the transmitting probe and the receiving probe so that the ultrasonic wave transmitted by the transmitting probe propagates in a part other than the sample but is not received by the receiving probe when the sample is a pipe, a plate or the like and has a constant thickness.

* * * * *